(12) United States Patent
Aiko et al.

(10) Patent No.: US 10,113,959 B2
(45) Date of Patent: Oct. 30, 2018

(54) TERAHERTZ WAVE GENERATING DEVICE AND SPECTROSCOPIC DEVICE USING SAME

(71) Applicant: Hitachi High-Technologies Corporation, Minato-ku, Tokyo (JP)

(72) Inventors: Kenji Aiko, Tokyo (JP); Kei Shimura, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 15/550,146

(22) PCT Filed: Mar. 3, 2015

(86) PCT No.: PCT/JP2015/056233
§ 371 (c)(1),
(2) Date: Aug. 10, 2017

(87) PCT Pub. No.: WO2016/139754
PCT Pub. Date: Sep. 9, 2016

(65) Prior Publication Data
US 2018/0031469 A1    Feb. 1, 2018

(51) Int. Cl.
*G01N 21/35* (2014.01)
*G02F 1/35* (2006.01)
(Continued)

(52) U.S. Cl.
CPC .......... *G01N 21/3581* (2013.01); *G02F 1/19* (2013.01); *G02F 1/3551* (2013.01);
(Continued)

(58) Field of Classification Search
CPC ...... G01N 21/3581; G01N 2201/06113; G02F 1/19; G02F 1/3551; G02F 2201/20; G02F 2203/13; H01S 3/0057; H01S 3/0092
See application file for complete search history.

(56) References Cited

U.S. PATENT DOCUMENTS

| 6,697,186 B2 | 2/2004 | Kawase et al. |
| 6,903,341 B2 | 6/2005 | Imai et al. |
| 2002/0024718 A1* | 2/2002 | Kawase ............... G02F 1/39 359/330 |

FOREIGN PATENT DOCUMENTS

| JP | 2002-72269 A | 3/2002 |
| JP | 2003-5238 A | 1/2003 |

(Continued)

OTHER PUBLICATIONS

International Search Report (PCT/ISA/210) issued in PCT Application No. PCT/JP2015/056233 dated Jun. 2, 2015 with English translation (Four (4) pages).

(Continued)

*Primary Examiner* — Mark R Gaworecki
(74) *Attorney, Agent, or Firm* — Crowell & Moring LLP

(57) ABSTRACT

A terahertz wave generating device according to the present invention comprises a fixed-wavelength pump optical laser that generates a single wavelength pump beam, a variable-wavelength laser that emits a seed beam and is capable of making the wavelength of the seed beam variable, a delay element that delays pulses of the pump beam and a first non-linear crystal that generates terahertz waves by receiving the seed beam, a first pump beam that is not delayed by the delay element and a second pump beam that is delayed by the delay element.

18 Claims, 6 Drawing Sheets

(51) Int. Cl.
  *G02F 1/19* (2006.01)
  *H01S 3/00* (2006.01)
  *G01N 21/3581* (2014.01)
  *G02F 1/355* (2006.01)

(52) U.S. Cl.
  CPC .......... *H01S 3/0057* (2013.01); *H01S 3/0092* (2013.01); *G01N 2201/06113* (2013.01); *G02F 2201/20* (2013.01); *G02F 2203/13* (2013.01)

(56) References Cited

FOREIGN PATENT DOCUMENTS

| JP | 2003-232906 A | 8/2003 |
|----|---------------|--------|
| JP | 2003-302666 A | 10/2003 |
| JP | 2004-163284 A | 6/2004 |
| JP | 2006-215222 A | 8/2006 |
| JP | 2014-81345 A | 5/2014 |

OTHER PUBLICATIONS

Japanese-language Written Opinion (PCT/ISA/237) issued in PCT Application No. PCT/JP2015/056233 dated Jun. 2, 2015 (Four (4) pages).

\* cited by examiner

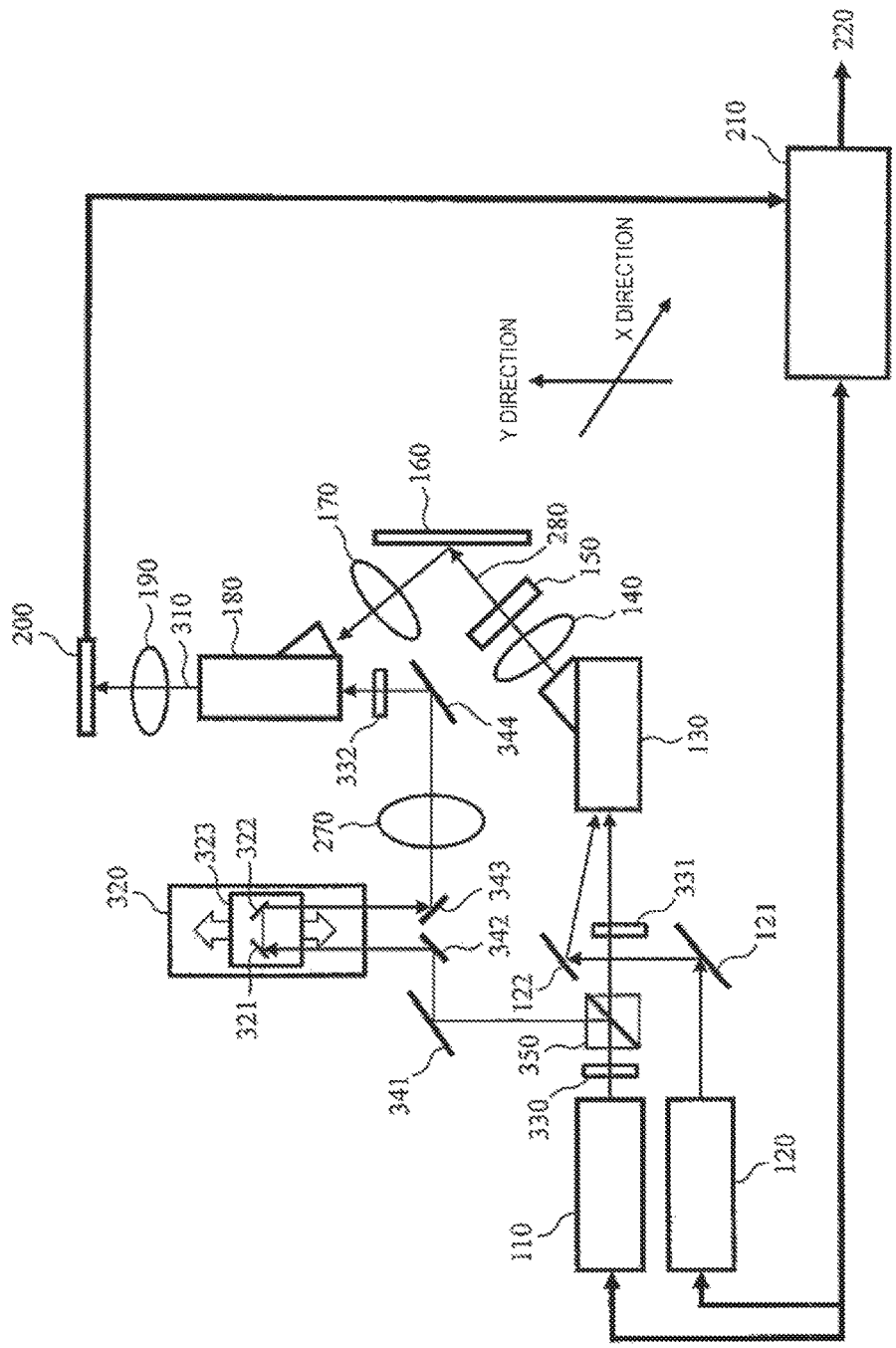
[Fig. 1]

[Fig. 2]
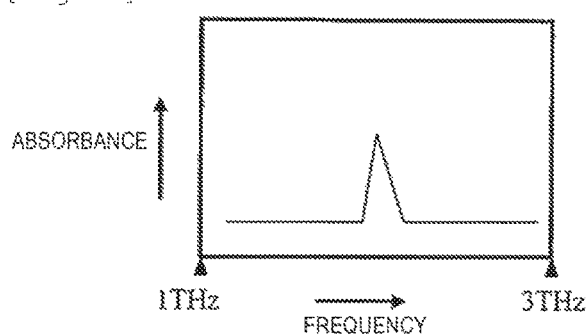
[Fig. 3]
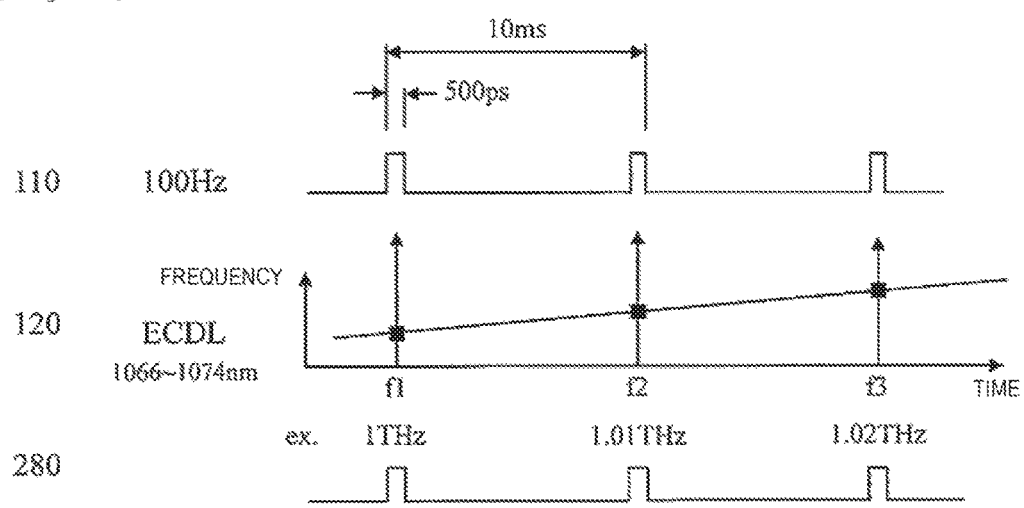

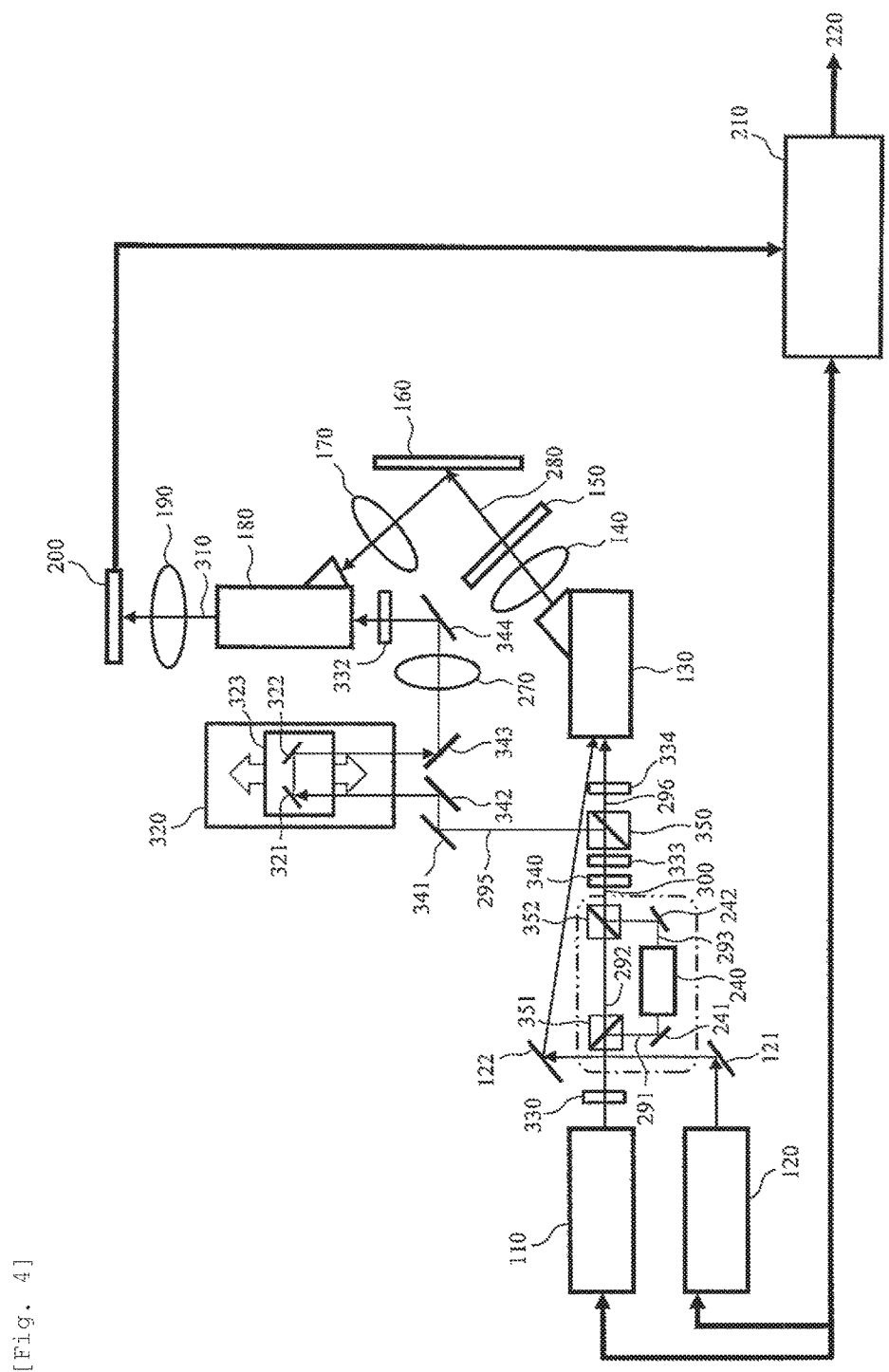
[Fig. 4]

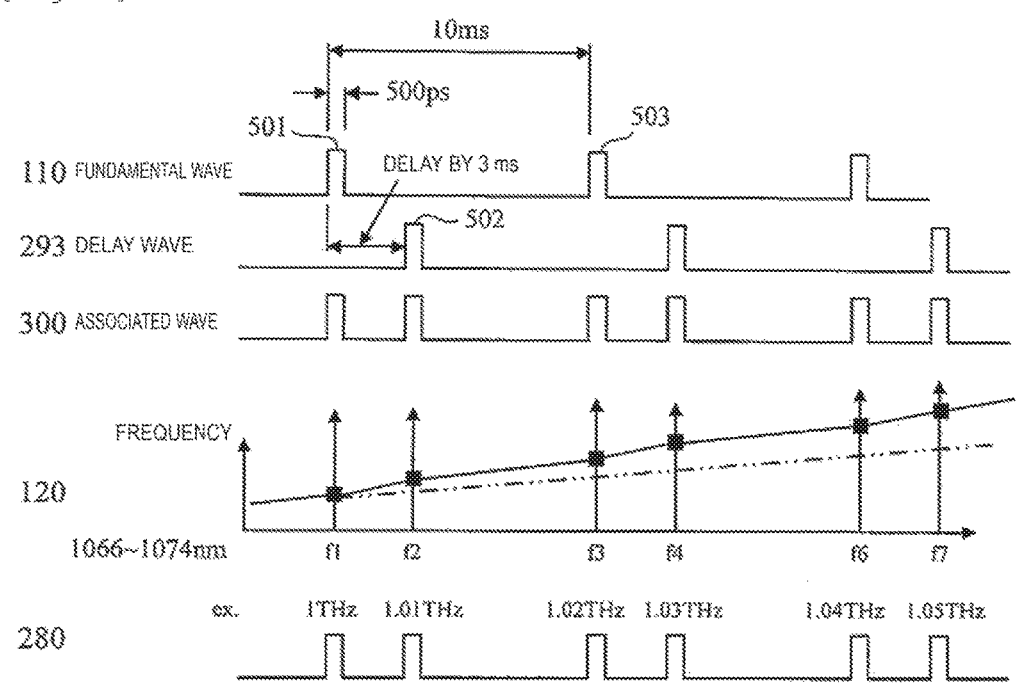

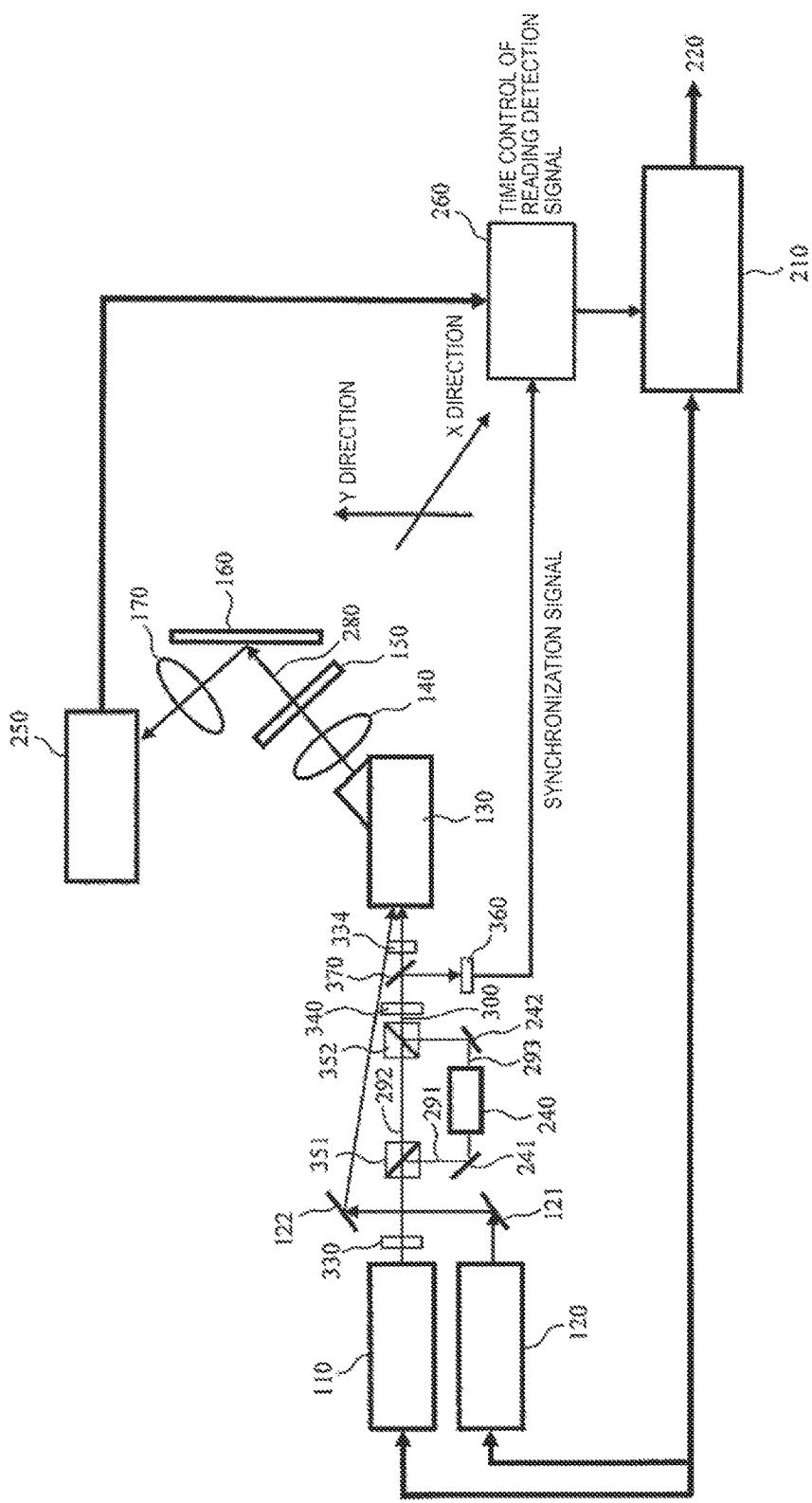

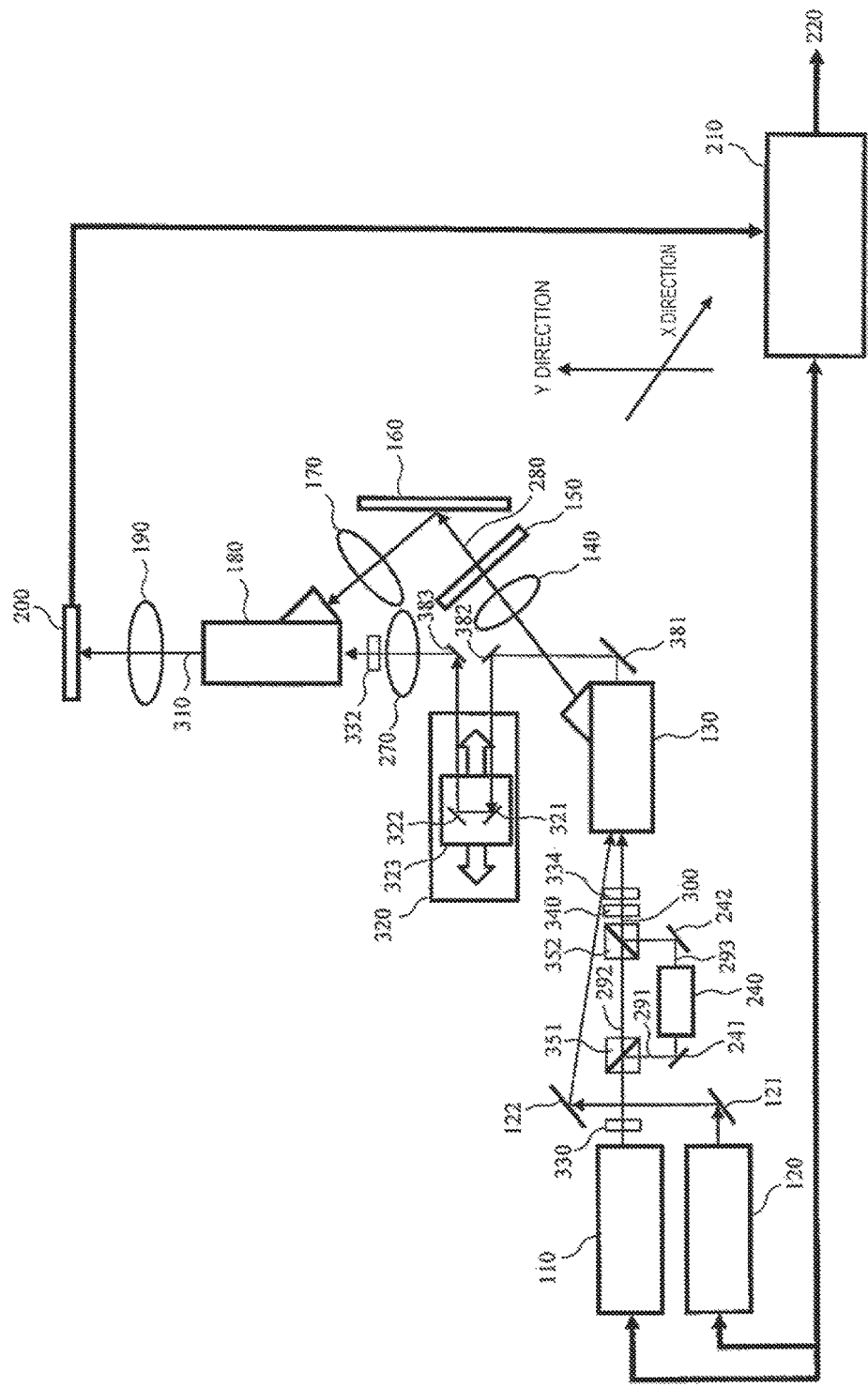
[Fig. 7]

TERAHERTZ WAVE GENERATING DEVICE AND SPECTROSCOPIC DEVICE USING SAME

TECHNICAL FIELD

The present invention relates to a terahertz wave generating device and a spectroscopic device using the same.

BACKGROUND ART

A far infrared region wave is an electromagnetic wave having a frequency range of approximately 0.1 THz to 10 THz. The far infrared region wave has excellent transmittance with respect to many types of materials, such as paper, wood, or plastic, compared to an infrared ray which is an electromagnetic wave having a higher frequency band, and has excellent straightness or resolving power compared to a millimeter wave which is an electromagnetic wave having a lower frequency band.

In addition, an intrinsic absorption spectrum of many types of materials starting from a high molecular compound, such as sugar or protein, is included in a frequency band of a far infrared wave. There is a method of observing a transmitted wave or a reflected wave by irradiating a target material with the far infrared region wave considering the characteristics.

According to the observation method, it is possible to observe an inner structure of the target, the presence or absence of a defect and foreign substances, a difference of materials or intrinsic components, or the like, in a non-destructive manner in a state where the target is in a container having transmittance. Therefore, it is assumed that the observation method can be employed in a material inspection, a structure inspection, or the medicine inspection.

As a generating method of a far infrared region wave of the related art, in 1990s, an optical source and a detector which has a small size, does not require cooling, and uses femtosecond laser were commercialized. At present, a general-purpose spectroscopic measuring device based on time-domain spectroscopy which used the method is commercially available.

Meanwhile, from approximately 2000, a compact coherent optical source of which a frequency is variable in a broadband has been actively studied, and high output characteristics have been developed. Furthermore, a detection technology which used non-linear crystal has also been developed.

In addition, at the same time as emission from high-output Q switch YAG laser, photoinjection (seed optical source) to the non-linear crystal is performed, and accordingly, it is possible to achieve narrowband of generated frequency in far infrared region light. According to the configuration, it is possible to realize both of a broadband and spectroscopic optical source of the narrowband, utilization as a general-purpose spectroscopic optical source widens.

CITATION LIST

Patent Literature

PTL 1: JP-A-2003-302666

SUMMARY OF INVENTION

Technical Problem

However, in the Q switch YAG laser of pulse laser which excites the non-linear crystal, from the viewpoint of ensuring lifespan and reliability, a driving frequency thereof is limited to approximately 100 Hz. The limited driving frequency restricts performance of a terahertz wave (for example, far infrared region light) generating device. For example, in a case where the terahertz wave generating device is employed in a general-purpose spectroscope, the restricted driving frequency causes restriction on a spectroscopic detection velocity.

Therefore, in order to further increase performance of the terahertz wave generating device, it is necessary to increase the velocity of the driving frequency (approximately 100 Hz) of the Q switch YAG laser (hereinafter, referred to as a pump optical laser), but as described above, the driving frequency of the current pump optical laser is restricted. Therefore, it is difficult to improve the driving frequency of the pump optical laser itself.

From above, it is necessary to improve generation efficiency of terahertz waves without changing the driving frequency of the pump optical laser.

Here, the present invention provides a technology which can improve generation efficiency of terahertz waves without changing a driving frequency of a pump optical laser.

Solution to Problem

In order to solve the above-described problem, for example, a configuration described in the range of claims is employed. The specification includes a plurality of means for solving the problem, but according to an example thereof, there is provided a terahertz wave generating device including: a fixed-wavelength pump optical laser that generates a single wavelength pump beam; a variable-wavelength laser that emits a seed beam and is capable of making the wavelength of the seed beam variable; a delay element that delays pulses of the pump beam; and a first non-linear crystal that generates terahertz waves by receiving the seed beam, a first pump beam that is not delayed by the delay element, and a second pump beam that is delayed by the delay element.

In addition, according to another example, there is provided a spectroscopic device including: a fixed-wavelength pump optical laser that generates a single wavelength pump beam; a variable-wavelength laser that emits a seed beam and is capable of making the wavelength of the seed beam variable; a delay element that delays pulses of the pump beam; a first non-linear crystal that generates terahertz waves by receiving the seed beam, a first pump beam that is not delayed by the delay element, and a second pump beam that is delayed by the delay element; and a detector which detects the terahertz wave with which a sample is irradiated.

Advantageous Effects of Invention

According to the present invention, it is possible to improve generation efficiency of terahertz waves without changing a driving frequency of a pump optical laser.

More characteristics related to the present invention will become apparent from the description and the attached drawings of the specification. In addition, other problems, configurations, and effects except for the above-described problems, configurations, and effects will be apparent by the description of the following examples.

BRIEF DESCRIPTION OF DRAWINGS

FIG. 1 is a schematic configuration view of a reference example of a far infrared spectroscopic device.

FIG. 2 is an example of spectral spectrum characteristics of a far infrared ray frequency and absorbance.

FIG. 3 is an example of a timing chart of generation of far infrared region waves.

FIG. 4 is a schematic configuration view of a far infrared spectroscopic device according to First Example.

FIG. 5 is an example of the timing chart of generation of the far infrared region waves according to First Example.

FIG. 6 is a schematic configuration view of a far infrared spectroscopic device according to Second Example.

FIG. 7 is a schematic configuration view of a far infrared spectroscopic device according to Third Example.

DESCRIPTION OF EMBODIMENTS

Hereinafter, examples of the present invention will be described with reference to the drawings. In addition, the attached drawings illustrate specific examples in accordance with a principle of the present invention, but these are for understanding the present invention, and are not used for limitedly interpreting the present invention by no means. Modification examples obtained by combining or replacing the following examples and known technologies are also included in the range of the present invention.

The following examples are related to a terahertz wave generating device. In general, a terahertz wave is an electromagnetic wave having a frequency of 0.1 THz to 100 THz. In addition, in the specification, the terahertz wave is defined as a wave which also includes an electromagnetic wave having tens of GHz to hundreds of THz.

The terahertz waves can be used in imaging, various measurement of a spectrometer or the like, or nondestructive inspection. Hereinafter, as an example, an example in which the terahertz wave generating device is employed in a far infrared spectroscopic device will be described, but it is also possible to employ the terahertz wave generating device in a device other than the far infrared spectroscopic device.

In addition, in the following description, a term "terahertz wave" is used as a term including a region of the above-described far infrared beam.

The far infrared spectroscopic device is used in an inspection process, such as an analysis of chemical material components distribution in a sample, or an inspection of foreign components or foreign substances. The spectroscopic device is a device which can perform a component analysis of the sample from the characteristics of a frequency, such as absorption spectrum, in transmitted beam which is transmitted through the sample or a reflected beam reflected from the beam by using the light of a far infrared region.

Reference Example

FIG. 1 is a schematic configuration view of a reference example of the far infrared spectroscopic device. As main configuration elements, the far infrared spectroscopic device includes two types of laser optical sources (a pump optical laser 110 and a variable-wavelength far infrared optical source 120), anon-linear crystal (first non-linear crystal) 130 for the optical source, an illumination optical system 140, a sample 150, a non-linear crystal (second non-linear crystal) 180 for detection, a photodetector 200, and a control portion 210 which performs a light-generation time control of laser and a spectral control of a detection signal.

Hereinafter, from the generation of a far infrared region wave (hereinafter, referred to as a far infrared beam), to the reception of the far infrared beam by a signal detection system (photodetector 200) will be described in detail.

As a configuration of a variable-wavelength optical source for generating the far infrared beam, there is a configuration in which the far infrared beam is generated by difference frequency generation or parametric generation which is generated when the non-linear crystal is irradiated with two types of laser beams.

For example, as the non-linear crystal 130, MgO:LiNbO3 is used. In addition, the pump optical laser 110 is a fixed-wavelength pump optical laser that generates a single wavelength pump beam, and for example, is a Q switch YAG laser having short pulses. The variable-wavelength far infrared optical source (hereinafter, referred to as a seed beam optical source) 120 is an optical source which can generate a seed beam having a desirable wavelength. The variable-wavelength far infrared optical source 120 can change the wavelength of the seed beam. More specifically, the wavelength of the seed beam may continuously change. Here, "desirable wavelength" means a wavelength within a range of specification of the laser that can make the wavelength variable. The seed beam is generated, and the wavelength of the seed beam is variable.

In the pump beam from the pump optical laser 110, an azimuth angle of linearly polarized beam changes by a half-wave plate (hereinafter, λ/2 plate) 330, and after this, the beam branches into the transmitted beam and the reflected beam by a polarization beam splitter (hereinafter, PBS) 350. The transmitted light passes through a λ/2 plate 331, and is incident on the non-linear crystal 130.

The seed beam from the seed beam optical source 120 is incident on the non-linear crystal 130 having a slight angle with the pump beam (transmitted beam which has been transmitted through the PBS 350) via two mirrors 121 and 122.

According to the configuration, when the seed beam from the seed beam optical source 120 goes into the non-linear crystal 130, it is possible to obtain far infrared beams having different wavelengths from each other by the parametric generation.

When attaching a Si prism to a desirable position on an outlet side of the far infrared beam of the non-linear crystal 130, it is possible to efficiently extract the generated far infrared beam. Here, the wavelength of the seed beam optical source 120 changes approximately from 1066 nm to 1076 nm, and in accordance with this, the beam is incident having an incident angle of the seed beam to the non-linear crystal 130 that is optimal within a range of approximately 2° to 4°. According to the configuration, it is possible to change the generation frequency of the far infrared beam to be generated within a range of 0.5 THz to 3 THz.

The far infrared beam obtained in this manner is adjusted to a desirable beam shape through the illumination optical system 140. The sample 150 which is a measurement target is irradiated with the adjusted beam.

When measuring a spectral spectrum of a part of the sample 150, a beam diameter with which the sample 150 is irradiated is narrowed down to approximately φ1 mm via the illumination optical system 140. As another example, when measuring an average spectral spectrum of the sample 150, the beam diameter is not narrowed down, and the sample 150 is irradiated with the beam having approximately φ10 mm.

In a case of narrowing down the beam, the far infrared spectroscopic device may include an XY stage (not illustrated) for loading the sample 150 which is the measurement target. By moving the sample 150 in a two-dimensional axial direction by the XY stage, it is also possible to obtain spectral spectrum information (map information) distributed in the two-dimensional direction.

As another example, the illumination optical system 140 may include a deflection portion for changing the irradiation direction of the beam. By changing the irradiation direction of the measurement beam by the deflection portion, and by scanning the sample 150 by the beam in a one-dimensional or two-dimensional direction, it is also possible to similarly acquire the spectral spectrum information (map information) distributed in the two-dimensional direction on the sample 150.

In this structure, when the far infrared beam is transmitted through the sample 150 which is the measurement target or reflected from the sample 150, there is a case where unique dependency characteristics of the frequency and the quantity of light are generated according to the material of the sample 150. Since the characteristics of the spectral spectrum show unique spectrum in a component of the sample 150, it can be said that the characteristics are a fingerprint of the material since the characteristics are led to identification of the component or the like of the material.

FIG. 2 is an example of spectral spectrum characteristics of a far infrared ray frequency and absorbance. As illustrated in FIG. 2, when showing the frequency of the far infrared beam on the horizontal axis and the absorbance (or transmissivity) on the vertical axis, the characteristics are easily understood.

The characteristics are shown for generating the absorption phenomenon in the spectral components of the transmitted beam or the reflected beam only in a specific frequency by an intermolecular interaction of the material. In addition to the intermolecular interaction, a molecule resonance phenomenon is generated due to a hydrogen bonding portion of the molecules, or the molecule resonance phenomenon is similarly caused by crystallinity (crystal mass) of the molecules, and thus, the adsorption spectrum is generated.

It is frequently reported that the resonance phenomenon caused by the crystallinity can be detected as a change in adsorption spectrum. For example, as the resonance phenomenon, in a medical product or the like, there is a resonance phenomenon related to a structure aspect of the molecules, such as a difference in crystal structure which is called a crystal polymorphism having high frequency of generation when being crystallized from liquid, a difference between crystallinity and non-crystallinity, and an optical isomer which becomes an aspect (so-called a symmetrically opposite structure) in which the crystal polymorphism is a mirror image.

Next, in order to obtain the strength information, in general, the far infrared beam which is transmitted through or reflected from the sample 150 is converted into a near infrared beam which is easily detected by the detector (photodetector 200) having a shape to be photoelectrically converted.

Specifically, a far infrared beam 280 which is transmitted through the sample 150 is reflected by a mirror 160. The shape of the reflected far infrared beam is adjusted by a detection optical system 170, and the reflected far infrared beam is incident on the non-linear crystal 180. At the same time when the far infrared beam 280 is incident on the non-linear crystal 180, a part (reflected beam reflected by the PBS 350) of the pump beam is incident on the non-linear crystal 180. By the conversion of the wavelength used in both of the far infrared beam and a part of the pump beam, the near infrared beam which is in the vicinity of 1066 nm to 1076 nm is generated. For example, as the non-linear crystal 180, LiNbO3 or MgO:LiNbO3 may be used.

The generated near infrared beam is detected. At this time, the beam shape of the near infrared beam is adjusted by a detection optical system 190, and the near infrared beam is photoelectrically converted by the photodetector 200 having a sensitivity with respect to the near infrared beam, and is detected as a detection signal. The control portion 210 controls the pump optical laser 110 and the seed beam optical source 120. In addition, the control portion 210 performs a spectrum control of the detection signal detected by the photodetector 200, and outputs spectrum information 220.

The photodetector 200 for the near infrared beam may be one light-receiving element, may be light-receiving elements (1D array detector) in which a plurality of light-receiving elements are one-dimensionally arranged, or may be a light-receiving element (2D array detector) in which the plurality of light-receiving elements are two-dimensionally arranged. The light-receiving elements for the near infrared beam have a high operation velocity, are inexpensive, are easy to handle, and have many types, and thus, the light-receiving elements for the near infrared beam are appropriate for industrial application.

In addition, the control portion 210 may include a display portion (display or the like) which displays frequency spectrum (spectrum information 220) that shows the information corresponding to the strength of the signals from the photodetector 200.

As described in the example, in a case where the wavelength of the far infrared beam is converted into the wavelength of the near infrared beam by using the non-linear crystal 180, since quantum energy (hv value, h: Planck's constant, v: far infrared ray frequency) of the far infrared beam is low, a part (reflected beam reflected by the PBS 350) of the pump beam branches by the PBS 350, and is incident on the non-linear crystal 180 after being adjusted. Specifically, a part (reflected beam reflected by the PBS 350) of the pump beam passes through a pump beam irradiation optical system 270, and is reflected by a mirror 344. At a part of the reflected pump beam, the azimuth angle is adjusted by a λ/2 plate 332, and the part of the reflected pump beam is incident on the non-linear crystal 180.

In a case of realizing the configuration, at the same timing as the timing of making the pulses of the far infrared beam (terahertz wave) 280 incident on the non-linear crystal 180, it is necessary to make the pulses of the laser (reflected beam reflected by the PBS 350) branched from the pump beam incident. In order to adjust the timing of synchronization, the far infrared spectroscopic device includes an optical path length correction stage 320.

The optical path length correction stage 320 includes a moving mechanism 323 including the plurality of mirrors 321 and 322. By moving the positions of the plurality of mirrors 321 and 322 by the moving mechanism 323, the optical path length of the laser (reflected beam reflected by the PBS 350) branched from the pump beam is adjusted, and the timing of making the beam incident on the non-linear crystal 180 is adjusted. The laser (reflected beam reflected by the PBS 350) branched from the pump beam is incident on the optical path length correction stage 320 via two mirrors 341 and 342, and the optical path length is adjusted. The laser which has passed through the optical path length correction stage 320 becomes incident on the pump beam irradiation optical system 270 through a mirror 343.

In a case where the Q switch YAG laser is used as the pump optical laser 110, the frequency of the seed beam optical source 120 is controlled in accordance with the driving frequency, and a far infrared beam which has a desirable single wavelength is obtained. In the measurement of the absorption spectrum of the sample, by setting the far infrared beam to gradually various frequency, the spectrum information 220 is obtained. The measurement time when obtaining the spectrum information 220 is determined by the driving frequency of the Q switch YAG laser (pump optical laser 110).

FIG. 3 is an example of a timing chart of generation of the far infrared region wave. FIG. 3 illustrates a configuration in which the far infrared beam having a corresponding frequency is generated from the frequency of the seed beam optical source 120 synchronized with 100 Hz.

For example, in a case where the driving frequency of the pump optical laser 110 is 100 Hz, the pulse interval is 10 msec. The control portion 210 controls emission of the seed beam from the seed beam optical source 120 and the frequency thereof, in synchronization with the driving of the pump optical laser 110. Here, the set frequency of the seed beam optical source 120 is set by 10 GHz. In the example of FIG. 3, the control portion 210 is synchronized with the driving of the pump optical laser 110, and controls the emission of the seed beam by frequencies f1, f2, . . . , fm. In addition, in the example of FIG. 3, the frequencies f1, f2, . . . , fm of the seed beam linearly change with respect to the time axis.

As illustrated in FIG. 3, the timing of pulses of the far infrared beam (terahertz wave) 280 is the same timing as that of the pulses of the laser of the pump optical laser 110, and the frequency of the far infrared beam 280 to be generated is set by 0.01 THz from 1 THz.

In the example of FIG. 3, in a case of obtaining the spectrum information from 1 to 3 THz, the number of times of measurement is 200. From above, the time required for the measurement becomes (2 THz/0.01 THz)×10 msec=2000 msec, and a time required is 2 seconds/1 scan.

There is a case where the transmissivity of the far infrared beam 280 is not excellent according to the type of the sample 150. In this case, when measuring the transmission spectral spectrum, an SN ratio becomes data which is not excellent. In this case, in order to improve the SN ratio, there is a case where the measurement is repeatedly executed and an average value from the accumulated data is acquired. For example, in a case of collecting the data of the average value by performing the measurement 100 times, the SN ratio can be improved by $(100)^{1/2}=10$ times, but the measurement time becomes 2 seconds×100 times=200 seconds. In other words, 3.3 minute/1 scan is achieved, and the measurement time becomes long.

In addition, as described above, the measurement of two-dimensional distribution (map) of the sample in which the XY stage is used is assumed. On the sample 150, in a case of collecting the data at (X direction) 100 locations×(Y direction) 100 locations=10000 locations, the measurement time becomes 2 seconds×10000 locations=20000 seconds (333 minutes, that is 5.5 hours), and it is required to shorten the time for industrial use.

First Example

FIG. 4 is a schematic configuration view of the far infrared spectroscopic device according to First Example. In FIG. 4, the same configuration elements as those of FIG. 1 will be given the same reference numerals, and the description thereof will be omitted.

The inventors have found a configuration in which the high-frequency driving of the terahertz wave is possible by using the pump optical laser 110 which is the same as that of the reference example of FIG. 1. Accordingly, it becomes possible to increase the velocity of the spectrum measurement in the far infrared spectroscopic device. In the Q switch YAG laser (pump optical laser 110), the pulse width by the pulse light generation (CCW light generation) is approximately 500 psec. However, the driving frequency at which the light generation is repeated is approximately 100 Hz, and the pulse interval is long to be 10 msec. Here, at the interval of 10 msec, pulses of the Q switch YAG laser is newly inserted.

In the example, in order to increase the velocity of generation of the far infrared beam, the terahertz wave generating device in the far infrared spectroscopic device makes a fundamental wave (pump beam from the pump optical laser 110) of 100 Hz branch, and generates a delay wave obtained by delaying one of the branched waves. The terahertz wave generating device overlaps the delay wave on the original fundamental wave, and generates an associated wave. By making the fundamental wave and the delay wave associated with each other, the frequency increases two times, and the velocity (efficiency) of generation of the far infrared region can increase two times.

Here, the original pulse width of the pump optical laser 110 is smaller than 1 nsec (pulse width<1 nsec). As an example, when the delay time is equal to or longer than 1 nsec (delay time≥1 nsec), the frequency of the associated wave can increase two times.

In order to generate the delay wave, it is possible to use the delay elements. For example, since the light velocity is $3×10^8$ m/sec, for 1 nsec, the beam advances by 0.3 m. A case where silicon (Si) of which a refractive index is n=3.41 is used as the delay element, is assumed. In this case, 0.3/3.41=0.088 m, and thus, it can be ascertained that one of the branched fundamental waves may be allowed to pass through the delay element (material) of which length>88 mm. As an example, with respect to the delay material having an intrinsic refractive index, the delay time may be adjusted by appropriately changing the length thereof.

In this manner, in an aspect of the generation of the far infrared region caused by excitation of dual wavelength laser, the branched excited layer passes through the delay element, the delay pulse wave is generated, and accordingly, the driving frequency of the pump optical laser 110 itself does not change, and it becomes possible to achieve a high frequency of the terahertz wave. Therefore, it becomes possible to achieve a high velocity of the spectrum analysis that uses variable frequency.

In addition, the fundamental wave may be branched into three or more waves, and two or more delay elements may be aligned in parallel. Accordingly, it becomes possible to achieve a high velocity three times or higher the generation velocity of the terahertz wave. In addition, in generating the terahertz wave from the non-linear crystal 130, it is necessary that the laser power for excitation exceeds an intrinsic threshold value of the crystal. When increasing the number of branches and the number of parallel alignments, the energy of the pulses of each of the laser beams is reduced. Therefore, it can be assumed that a limit of achieving a high velocity in this method is laser power dependency.

As illustrated in FIG. 4, specifically, the irradiation optical path of the pump optical laser is divided into the irradiation optical path and a branched optical path. The pump beam which advances the branched optical path returns to the original irradiation optical path after being delayed only by a predetermined time, and overlaps the pump beam which is not delayed. The non-linear crystal is irradiated with the overlapping pump beam.

In order to achieve the description above, the terahertz wave generating device in the far infrared spectroscopic device includes an optical element which makes the irradiation optical path of the pump optical laser 110 branch, a delay element 240 disposed on the branched optical path, and an optical element for overlapping the pump beam in the original irradiation optical path and the pump beam delayed by the delay element.

In a rear step of the pump optical laser 110, a λ/2 plate 330 is disposed. First, regarding the pump beam output from the pump optical laser 110, the azimuth angle of the linearly polarized beam is changed by the λ/2 plate 330. In a rear step of the λ/2 plate 330, a polarization beam splitter (hereinafter, referred to as PBS) 351 is disposed. As the pump beam branches by the PBS 351, the quantity of light of a reflected wave (beam branched to the delay element 240) 291 and the quantity of light of a transmitted wave 292 are adjusted.

On the branched optical path, a mirror 241 is disposed, and the reflected wave 291 is reflected by the mirror 241 and is guided to the delay element 240. The delay element 240 gives a predetermined delay time to the pulses of the reflected wave 291, and generates a delay wave 293 delayed by a transmission time. The delay wave 293 is reflected by a mirror 242, and is incident on a PBS 352.

The PBS 352 is disposed on the original irradiation optical path. The transmitted wave (first pump beam) 292 and the delay wave (second pump beam) 293 overlap each other via the PBS 352. The overlapping optical wave (hereinafter, associated wave 300) is incident on a polarizing plate 340 disposed at the rear step of the PBS 352. Regarding the associated wave 300, the polarized beams having the same azimuth angle are extracted from the polarization components which go straight to each other by the polarizing plate 340. After this, the associated wave 300 is transmitted through a λ/2 plate 333, and a desirable azimuth angle is achieved.

Next, a spectrum ratio of the associated wave 300 is adjusted by the PBS 350. The associated wave 300 branches into a reflected wave (a beam oriented toward the non-linear crystal 180 via the optical path length correction stage 320) 295 and a transmitted wave (a beam oriented toward the non-linear crystal 130) 296 by the PBS 350. In order to make the transmitted wave 296 incident on the non-linear crystal 130, the azimuth angle (direction perpendicular to S polarized beam and the paper surface) is adjusted by a λ/2 plate 334.

The optical path length of the reflected wave 295 is adjusted by the optical path length correction stage 320. Accordingly, the timing at which the pulses of the reflected wave 295 is incident on the non-linear crystal 180 becomes identical to the timing at which the pulses of the far infrared beam (terahertz wave) 280 to be generated is incident on the non-linear crystal 180. In addition, in the example, the mechanism for adjusting the optical path length (optical path length correction stage 320) is disposed at a front step of the pump beam irradiation optical system 270, but the mechanism may be disposed at the rear step of the pump beam irradiation optical system 270.

In addition, similar to the configuration of FIG. 1, the seed beam from the seed beam optical source 120 is incident on the non-linear crystal 130 having a slight angle with the transmitted wave 296 which has been transmitted through the PBS 350, via the two mirrors 121 and 122.

In the example, the control portion 210 controls the emission of the seed beam from the seed beam optical source 120 and the frequency (or the wavelength) thereof in synchronization with the timing of the pulses of the associated wave 300. For example, the set frequency of the seed beam optical source 120 is set by 10 GHz. As described above, by the configuration of the delay element 240, the delay time of the delay wave 293 can be calculated in advance. Therefore, the timing of the pulses of the associated wave 300 can be calculated in advance. In the control portion 210, the timing of the pulses of the associated wave 300 is set in advance. The control portion 210 controls the emission of the seed beam at frequencies f1, f2, . . . , fm in synchronization with the timing of the pulses of the associated wave 300.

In addition, processing after the associated wave 300 branches by the PBS 350 is the same as that of FIG. 1, and the description thereof will be omitted. A part (reflected beam reflected by the PBS 350) of the associated wave 300 and the far infrared beam 280 are incident on the non-linear crystal 180 at the same timing. In the non-linear crystal 180, the wavelength of the far infrared beam is converted into the wavelength of the near infrared beam. In addition, the near infrared beam is detected as the detection signal by the photodetector 200 having a sensitivity with respect to the near infrared beam. The display portion connected to the control portion 210 displays the frequency spectrum which shows the information corresponding to the strength of the signal from the photodetector 200 with respect to the frequency of the far infrared beam (terahertz wave) 280.

According to the above-described configuration, a part of the laser from the pump optical laser 110 branches and is delayed, and the delayed laser beam overlaps the laser beam before being branched. Accordingly, it is possible to increase the number of pulses of light generation two times (associated wave 300).

FIG. 5 is an example of the timing chart of generation of the far infrared region waves according to First Example, and describes an example in which the delay wave delayed by 3 msec is generated. The example of FIG. 5 is similar to that of FIG. 3, and the driving frequency of the pump optical laser 110 is 100 Hz, and the pulse interval is 10 msec. The delay time by the delay element 240 is set to be 3 msec.

As illustrated in FIG. 5, the pulses of the associated wave 300 are generated at the timing of the pulse of the pump beam (first pump beam) from the pump optical laser 110 and at the timing of the pulse of the delay wave 293 (second pump beam), and the generation of the pulses is repeated.

The interval of the associated wave 300 between the pulse of the pump beam (first pump beam) from the pump optical laser 110 and the pulse of the delay wave 293 (second pump beam) is a non-equal interval. For example, while the interval between a pulse 501 of the first pump beam and a pulse 502 of the second pump beam is 3 msec, the interval between the pulse 502 of the second pump beam and a pulse 503 of the first pump beam is 7 msec.

In addition, the delay time delayed by the delay element 240 is 3 msec, and the period of the pump beam from the pump optical laser 110 is 10 msec. Therefore, the delay time delayed by the delay element 240 is shorter than a half (5 msec) of the period of the pump beam from the pump optical laser 110. In this manner, the delay wave 293 makes the transmitted wave (fundamental wave) 292 of the pump beam from the pump optical laser 110 associated with the fundamental wave in a slightly shifted state.

In addition, when the pulse width of the pump beam from the pump optical laser 110 is 500 psec, the delay time may be approximately 1 nsec. Therefore, the delay time delayed by the delay element 240 may be longer than the pulse width of the pump beam from the pump optical laser 110, and for example, may be two times or longer the pulse width of the pump beam from the pump optical laser 110.

The period of the pump beam from the pump optical laser 110 may be two times or longer the pulse width of the pump beam from the pump optical laser 110. In the example, the pulse width of the pump beam from the pump optical laser 110 is approximately 500 psec, and the period of the pump beam from the pump optical laser 110 is 10 msec. Therefore, the period of the pump beam from the pump optical laser 110 is $10^7$ times or longer the pulse width of the pump beam from the pump optical laser 110. Therefore, the period of the pump beam from the pump optical laser 110 may be $10^n$ (for example, $1 \leq n \leq 7$) times or longer the pulse width of the pump beam from the pump optical laser 110.

As described above, the example uses characteristics that the pulse width of the terahertz waves is short. For example, in a case of an optical wave having a large pulse width, a longer delay time is required, and as a result, there is a problem that the size of the delay element increases. Meanwhile, since the pulse width of the terahertz wave is short, the delay wave may be slightly shifted with respect to the fundamental wave. In other words, there is no necessity that the delay wave is shifted exactly by a half with respect to the period of the fundamental wave. In the example, there are characteristics that it is possible to achieve a high frequency of the terahertz wave generating device by generating the associated wave of the fundamental wave and the delay wave which is slightly shifted from the fundamental wave.

In other words, since the pulse width of the terahertz wave is short, the delay time for generating the delay wave may be extremely short. For example, since the pulse width of the pump beam from the pump optical laser 110 is approximately 500 psec, the delay time may be approximately 1 nsec, and the delay time becomes extremely short. Since the period of the pump beam from the pump optical laser 110 is extremely long compared to the pulse width of the pump beam, a degree of freedom of inserting the delay wave into one period is also high. For example, since the pulse width of the pump beam is small and the delay time is short, it is also possible to insert a plurality of delay waves into the pump beam, and to perform the driving at a higher frequency by branching the beam into many steps. At this time, it is also possible to insert the plurality of delay waves into a half of the period of the fundamental wave.

The control portion 210 controls the frequency (or the wavelength) of the seed beam from the seed beam optical source 120 in accordance with the delay time delayed by the delay element 240. Specifically, as illustrated in FIG. 5, the control portion 210 controls the emission of the seed beam by the frequencies f1, f2, . . . , fm, in synchronization with the timing of the pulses of the associated wave 300. In addition, f1<f2<f3 . . . <fm.

In addition, the frequency of the far infrared beam 280 to be generated is set by 0.01 THz from 1 THz. In other words, the first terahertz wave generated by the first wavelength seed beam (seed beam which corresponds to the frequency f1) and the first pump beam 501, and the second terahertz wave generated by the second wavelength seed beam (seed beam which corresponds to the frequency f2) and the delay wave (second pump beam) 502, have different wavelengths from each other.

In the control portion 210, for example, the timing of the pulse of the associated wave 300 illustrated in FIG. 5 and the frequencies f1, f2, . . . , fm at each timing may be set in advance. In the example of FIG. 5, the frequencies f1, f2, . . . of the seed beam are set to non-linearly change with respect to the time axis in accordance with the timing of the pulse of the associated wave 300. In addition, the frequencies f1, f2, . . . of the seed beam may curvedly change with respect to the time axis.

In a case of being delayed by 3 msec, the driving frequency of 100 Hz of the pump optical laser 110 which is incident on the non-linear crystal 130 can be 200 Hz which is two times higher. At this time, the time which is variable according to 1 to 3 THz can be reduced by half, and the detection time can be shortened. Furthermore, by making the delay element 240 into multiple steps, it is possible to multiplex the delay time. For example, when two delay elements are disposed and the fundamental wave branches into three, it is possible to realize a driving frequency three times higher. In other words, the driving frequency of 100 Hz of the pump optical laser 110 can be 300 Hz which is three times higher. In addition, since attenuation of the laser strength caused by the division is generated, it is possible to assume that it becomes necessary to ensure a conversion threshold value in the non-linear crystal 130.

Next, the delay element 240 will be described hereinafter. When the pulse width caused by the pulse light generation (CCW light generation) is set to be 500 psec, when the delay time is approximately 1 nsec, it is possible to increase the frequency of the associated wave two times higher.

For example, the light velocity is $3 \times 10^8$ m/sec, and the beam advances by a distance of 0.3 m/1 nsec. As the delay element 240, in a case of using the material having a refractive index of n=3.41, 0.3 m/3.41=0.088 m. Therefore, the delay element (material) 240 of which the length>88 mm may be allowed to pass through.

In the above-described example, the refractive index of the delay element 240 is assumed to be n=3.14, but the delay element 240 is not limited to an element having a fixed value in this manner, and an element having an electric optical effect in which the refractive index is changed by the applied voltage, that is, an element of which the refractive index can be variable, for example, an element having a Pockels effect, an element having a Kerr effect or the like, can be used. By using the elements, it is possible to suppress delay time by controlling the voltage, and to control the timing of the delay time of the pulse.

In addition, in a case of using the above-described elements, a voltage control portion (not illustrated) which applies the voltage is connected to the delay element 240. The voltage control portion controls the delay time caused by the delay element 240 by controlling the applied voltage to the delay element 240. In this case, the control portion 210 is electrically connected to the delay element 240 or the voltage control portion. The control portion 210 is configured to monitor the applied voltage to the delay element 240. The control portion 210 calculates the delay time caused by the delay element 240 in accordance with the monitoring result of the applied voltage, and controls the frequencies f1, f2, . . . , fm of the seed beam in accordance with the timing of the pulse of the associated wave 300. In addition, the control portion 210 may be have a function of the above-described voltage control portion.

According to the above-described configuration, it is possible to realize the terahertz wave generating device which can perform the high-frequency driving at non-equal interval. In the structure in which the two types of laser beam (the pump beam and the seed beam) are incident on the non-linear crystal and the far infrared region wave is generated, the efficiency of generation of the terahertz wave depends on the driving frequency of the pump optical laser, but in the example, it is possible to improve the efficiency of generation of the terahertz wave without changing the driving frequency of the pump optical laser. Therefore, in a case where the terahertz wave generating device of the example is employed in the far infrared spectroscopic device, it is possible to increase the efficiency of generation of the far infrared region wave, and to shorten the spectrum measurement time.

In the above-described example, an example in which the Q switch YAG laser is used as the pump optical laser 110, the frequency thereof is 100 Hz, and the pulse width is 500 psec is described, but the method can be employed even when the laser frequency is much higher.

In the above-described method, in a case where a time difference between the pulse interval time determined by the frequency of the laser and the pulse width is large, it is possible to achieve a high frequency of the driving frequency by branching, delaying, and associating the above-described beams.

In addition, in the example, an example in which the Q switch YAG laser having a short pulse is used as the pump optical laser 110 is described, but the line width of the spectrum which becomes a fundament may be narrow, and thus, a mode-locking laser may be used. Since the laser also depends on the type of which the repetition is fast, there is also a case where the high-speed measurement becomes possible.

In addition, in a case of associating the delay wave (pulse wave) delayed only by a certain time by the delay element 240 with the fundamental wave and generating the associated wave, it is possible to increase the driving frequency. However, the interval between the pulse of the fundamental wave and the pulse of the delay wave is determined by the condition of the delay element 240. Therefore, there is a case where the interval between the pulse of the fundamental wave and the pulse of the delay wave is not constant. Due to this, the control portion 210 is configured so as to make the frequency of the seed beam optical source 120 variable in accordance with the pulse of the associated wave 300.

In the above-described example, after branching the fundamental wave into two and delaying one of the branched beams only by a predetermined time, the fundamental wave is associated, and the driving frequency two times higher is obtained. According to another example, the fundamental wave branches into three, and two delay elements having different delay time with respect to the two among the three branched beams are disposed. In addition, the two delay waves generated from the two delay elements and the fundamental wave are associated with each other. Accordingly, it is also possible to obtain a driving frequency three times higher. In this manner, it is possible to make the fundamental wave branch into multiple steps, to set the delay times to be different from each other with respect to each of the branched beams, and to generate the associated wave thereof.

In addition, the restriction condition of increasing of the driving frequency amplifier can be assumed that power-down caused by the branching of the fundamental wave from the pump optical laser 110 (Q switch YAG laser) is less than the wavelength conversion threshold value in the non-linear crystal 130. When the laser power which is incident on the non-linear crystal 130 is less than the threshold value, it is not possible to generate the terahertz wave from the non-linear crystal 130, and thus, the laser power cannot be used as an optical source for generation of the terahertz wave. Therefore, the number of branches that can ensure pulse energy that exceeds the threshold value becomes the maximum number of branches by the method, and it can be assumed that the frequency becomes the highest driving frequency.

Second Embodiment

FIG. 6 is a schematic configuration view of a far infrared spectroscopic device according to Second Example. The example is a far infrared spectroscopic device which can directly detect the far infrared beam.

In First Example, it is necessary to make the pump beam branch and to control the incidence timing of the associated beam and the terahertz wave onto the non-linear crystal 180, but in the example, since the far infrared beam is directly detected without conversion, the branching and controlling are not necessary. In other words, in the example of FIG. 6, configurations necessary in FIG. 1, for example, the branch (branch by the PBS 350) of the pump beam, the optical path length correction stage 320, and the non-linear crystal 180 become unnecessary.

In recent years, an element (far infrared region detector 250) which can directly detect the far infrared beam has been developed. As illustrated in FIG. 6, the far infrared region detector 250 is disposed at the rear step of the detection optical system 170. In the configuration, the far infrared beam 280 which is transmitted through the sample 150 is reflected by the mirror 160, the shape of the reflected far infrared beam is adjusted by the detection optical system 170, and the reflected far infrared beam is incident on the far infrared region detector 250.

In addition, in a case where the far infrared region detector 250 is a detection element of a bolometer system which performs heat conversion, the detection element has a time constant of msec order from the viewpoint of a structure. Therefore, the high velocity of the driving frequency of the pump optical laser 110 becomes possible only in the time restriction of the time constant of the bolometer.

According to the example, since the frequency of the far infrared beam is not converted by the non-linear crystal 180, it is advantageous that it is not necessary to make the pump beam branch and it is not necessary to control the incidence timing of the associated wave and the terahertz wave onto the non-linear crystal 180. Therefore, it becomes possible to detect the far infrared beam by a simple configuration compared to First Example.

Meanwhile, in the example, in order to reduce the noise, it is preferable to perform a lock-in control with the driving signal. Therefore, the far infrared spectroscopic device includes a lock-in control portion (lock-in amplifier) 260. The lock-in control portion 260 performs the control of reading the detection signal from the far infrared region detector 250. Specifically, the lock-in control portion 260 performs a time control of monitoring the branched beams (synchronization signal) from the associated wave 300, and reading the detection signal from the far infrared region detector 250.

In order to make the associated wave 300 branch, a beam sampler 370 is disposed at the rear step of a polarizing plate 340. The beam sampler 370 makes a part of the associated wave 300 branch. The branched part of the associated wave 300 is detected by a light-receiving element 360. The lock-in control portion 260 lock-in-controls the detection signal from the far infrared region detector 250 considering the detection signal detected by the light-receiving element 360 as the synchronization signal. By the configuration, it is possible to make it difficult to receive an influence of noise.

In addition, in the example, a case where the lock-in control is employed in the configuration in which the far infrared beam is directly detected is described, but the configuration of the lock-in control can also be employed in First Example and in Third Example which will be described hereinafter. In a case of employing the lock-in control, the detection with higher sensitivity becomes possible.

Third Embodiment

FIG. 7 is a schematic configuration view of the far infrared spectroscopic device according to Third Example. In First Example, the pump beam before being incident on the non-linear crystal 130 branches, but in the example, the pump beam after passing through the non-linear crystal 130 is used.

As illustrated in FIG. 7, at the rear step of the non-linear crystal 130, a mirror 381 is disposed. The associated wave 300 (associated wave of the transmitted wave 292 and the delay wave 293) which has passed through the non-linear crystal 130 is incident on the optical path length correction stage 320 via a mirror 382. The associated wave 300 which passes through the optical path length correction stage 320 becomes incident on the pump beam irradiation optical system 270 via a mirror 383. Other configurations are the same as those of FIG. 1.

According to the example, compared to a method of making the beam branch before the non-linear crystal 130 of FIG. 4, it is possible to use the entire quantity of the pump beam from the pump optical laser 110 in generation of the terahertz wave by the non-linear crystal 130. Therefore, it is possible to reduce a loss of laser beam for generating the terahertz wave, and to build a terahertz wave generating device having excellent efficiency.

In addition, the present invention is not limited to the above-described examples, and include various modification examples. For example, the above-described examples are described in detail for describing the present invention to be easily understood, and is not necessarily limited to an example in which all of the described configurations are provided. In addition, a part of the configuration of a certain example can be replaced with a configuration of other examples, and a configuration of other examples can also be added to a configuration of a certain example. In addition, with respect to a part of the configurations of each of the examples, it is possible to add, remove, and replace other configurations.

Functions of the control portion 210 or the like of the example may be realized by a program code of software. In this case, a storage medium which records the program code therein is provided in a system or a device, and a computer (or CPU or MPU) of the system or the device reads the program code stored in the storage medium. In this case, the program code itself read from the storage medium realizes the functions of the above-described examples, and the program code itself and the storage medium which stores the program code therein configure the present invention. As the storage medium for supplying the program code, for example, a flexible disk, a CD-ROM, a DVD-ROM, a hard disk, an optical disk, a magneto-optical disk, a CD-R, a magnetic tape, a nonvolatile memory card, or a ROM is used.

Finally, the process and the technology described here are essentially not related to any specific device, and can also be implemented by any corresponding combination of the components. Furthermore, multiple types of general-purpose devices can be used. In order to implement the steps of the method described here, there is also a case where it is advantageous to build a dedicated device. In other words, a part or the entirety of various functions of the control portion 210 or the like is realized by hardware that uses electronic components, such as integrated circuit.

Furthermore, in the above-described embodiment, control lines or information lines which are considered to be necessary for the description are illustrated, and the control lines or information lines do not necessarily illustrate all of the control lines or information lines for the product. All of the configurations may be connected to each other.

REFERENCE SIGNS LIST

110: PUMP OPTICAL LASER
120: VARIABLE-WAVELENGTH FAR INFRARED OPTICAL SOURCE (SEED BEAM OPTICAL SOURCE)
121: MIRROR
122: MIRROR
130: NON-LINEAR CRYSTAL
140: ILLUMINATION OPTICAL SYSTEM
150: SAMPLE
160: MIRROR
170: DETECTION OPTICAL SYSTEM
180: NON-LINEAR CRYSTAL
190: DETECTION OPTICAL SYSTEM
200: PHOTODETECTOR
210: CONTROL PORTION
220: SPECTRUM INFORMATION
240: DELAY ELEMENT
241, 242: MIRROR
250: FAR INFRARED REGION DETECTOR
260: LOCK-IN CONTROL PORTION
270: PUMP BEAM IRRADIATION OPTICAL SYSTEM
320: OPTICAL PATH LENGTH CORRECTION STAGE
321, 322: MIRROR
323: MOVING MECHANISM
330, 331, 332, 333, 334: HALF-WAVE PLATE ($\lambda/2$ PLATE)
340: POLARIZING PLATE
341, 342, 343, 344: MIRROR
350, 351, 352: POLARIZATION BEAM SPLITTER (PBS)
360: LIGHT-RECEIVING ELEMENT
370: BEAM SAMPLER
381, 382, 383: MIRROR

The invention claimed is:
1. A terahertz wave generating device comprising:
a fixed-wavelength pump optical laser that generates a single wavelength pump beam;
a variable-wavelength laser that emits a seed beam and is capable of making the wavelength of the seed beam variable;
a delay element that delays pulses of the pump beam;
a first non-linear crystal that generates terahertz waves by receiving the seed beam, a first pump beam that is not delayed by the delay element, and a second pump beam that is delayed by the delay element; and
a control portion which controls the wavelength of the seed beam output from the variable-wavelength laser in accordance with the time by which the second pump beam is delayed by the delay element.

2. The terahertz wave generating device according to claim 1,
wherein a frequency of the seed beam output from the variable-wavelength laser non-linearly changes with respect to the time.

3. The terahertz wave generating device according to claim 1,
wherein an interval of pulses of an associated wave of the first pump beam and the second pump beam is a non-equal interval.

4. The terahertz wave generating device according to claim 1,
wherein a period of the first pump beam is two times or longer a pulse width of the first pump beam.

5. The terahertz wave generating device according to claim 4,
wherein time by which the second pump beam is delayed by the delay element is shorter than a half of the period of the first pump beam.

6. The terahertz wave generating device according to claim 1,
wherein the delay element is a delay material having an intrinsic refractive index.

7. The terahertz wave generating device according to claim 1,
wherein the delay element is an element in which the refractive index is changed by an applied voltage, and
wherein the device further comprises a control portion which controls the wavelength of the seed beam output from the variable-wavelength laser by monitoring the applied voltage.

8. The terahertz wave generating device according to claim 1, further comprising:
a detector which detects the terahertz wave with which a sample is irradiated;
a lock-in amplifier which controls reading timing of signals from the detector based on timing of the pulse generation of the associated wave of the first pump beam and the second pump beam.

9. The terahertz wave generating device according to claim 1, further comprising:
a second non-linear crystal which generates a near infrared beam as the terahertz wave with which the sample is irradiated and the first pump beam or the second pump beam are incident on the second non-linear crystal,
wherein the first pump beam or the second pump beam after passing through the first non-linear crystal is incident on the second non-linear crystal.

10. The terahertz wave generating device according to claim 1,
wherein a first terahertz wave generated by a first wavelength seed beam and the first pump beam, and a second terahertz wave generated by a second wavelength seed beam and the second pump beam, have different wavelengths.

11. The terahertz wave generating device according to claim 10, comprising:
a detector which detects a transmitted beam or a reflected beam which is generated by irradiating the sample with the first terahertz waves and the second terahertz wave; and
a display portion which displays a frequency spectrum that shows information corresponding to strength of a signal from the detector with respect to the frequency of the terahertz wave.

12. A spectroscopic device comprising:
a fixed-wavelength pump optical laser that generates a single wavelength pump beam;
a variable-wavelength laser that emits a seed beam and is capable of making the wavelength of the seed beam variable;
a delay element that delays pulses of the pump beam;
a first non-linear crystal that generates terahertz waves by receiving the seed beam, a first pump beam that is not delayed by the delay element, and a second pump beam that is delayed by the delay element;
a control portion which controls the wavelength of the seed beam output from the variable-wavelength laser in accordance with the time by which the second pump beam is delayed by the delay element; and
a detector which detects the terahertz wave with which a sample is irradiated.

13. The spectroscopic device according to claim 11,
wherein a frequency of the seed beam output from the variable-wavelength laser non-linearly changes with respect to the time.

14. The spectroscopic device according to claim 11,
wherein an interval of pulses of an associated wave of the first pump beam and the second pump beam is a non-equal interval.

15. The spectroscopic device according to claim 11,
wherein a period of the first pump beam is two times or longer a pulse width of the first pump beam.

16. The spectroscopic device according to claim 15,
wherein time by which the second pump beam is delayed by the delay element is shorter than a half of the period of the first pump beam.

17. The spectroscopic device according to claim 11, further comprising:
a lock-in amplifier which controls reading timing of signals from the detector based on timing of the pulse generation of the associated wave of the first pump beam and the second pump beam.

18. The spectroscopic device according to claim 11, further comprising:
a second non-linear crystal which generates near infrared beam as the terahertz wave with which the sample is irradiated and the first pump beam or the second pump beam are incident on the second non-linear crystal,
wherein the first pump beam or the second pump beam after passing through the first non-linear crystal is incident on the second non-linear crystal, and
wherein the detector detects the near infrared beam.

* * * * *